United States Patent
Buckner

(10) Patent No.: US 10,213,471 B1
(45) Date of Patent: Feb. 26, 2019

(54) METHOD FOR MAKING A PAIN RELIEVER OIL

(71) Applicant: Vanessa R. Buckner, Florissant, MO (US)

(72) Inventor: Vanessa R. Buckner, Florissant, MO (US)

( * ) Notice: Subject to any disclaimer, the term of this patent is extended or adjusted under 35 U.S.C. 154(b) by 0 days.

(21) Appl. No.: 15/722,925

(22) Filed: Oct. 2, 2017

Related U.S. Application Data

(60) Provisional application No. 62/415,643, filed on Nov. 1, 2016.

(51) Int. Cl.
| | | |
|---|---|---|
| A61K 36/81 | (2006.01) |
| A61K 33/14 | (2006.01) |
| A61K 47/44 | (2017.01) |
| A61K 36/28 | (2006.01) |
| A61K 36/53 | (2006.01) |
| A61K 36/88 | (2006.01) |
| A61K 36/9066 | (2006.01) |
| A61K 36/9068 | (2006.01) |
| A61K 36/67 | (2006.01) |
| A61K 36/61 | (2006.01) |

(52) U.S. Cl.
CPC .......... *A61K 36/81* (2013.01); *A61K 33/14* (2013.01); *A61K 36/28* (2013.01); *A61K 36/53* (2013.01); *A61K 36/61* (2013.01); *A61K 36/67* (2013.01); *A61K 36/88* (2013.01); *A61K 36/9066* (2013.01); *A61K 36/9068* (2013.01); *A61K 47/44* (2013.01); *A61K 2236/35* (2013.01)

(58) Field of Classification Search
None
See application file for complete search history.

(56) References Cited

U.S. PATENT DOCUMENTS

| | | |
|---|---|---|
| 4,997,853 A | 3/1991 | Bernstein |
| 8,932,656 B1 | 1/2015 | Henderson |
| 9,023,325 B2 | 5/2015 | Florence et al. |

OTHER PUBLICATIONS

Amruthraj et al. Effect of Vegetable Oil in the Solubility of capsaicinoids extracted from Capsicum Chinese Bhut Jolokia, vol. 7, Suppl 1, 2004.*
How to Make a Calendula Oil Infusion [online]. Root Simple, Jul. 23, 2011. Retrieved from the Internet: <URL: www.rootsimple.com/2011/07/howtomakeacalendulaoilinfusion/>.

* cited by examiner

*Primary Examiner* — Robert A Wax
*Assistant Examiner* — Melissa S Mercier
(74) *Attorney, Agent, or Firm* — Creativenture Law, LLC; Dennis J M Donahue, III; Kevin C. Staed

(57) ABSTRACT

A pain reliever oil made of a mixture of dried flower oil extract, carrier oils, magnesium oil, spice oil extract, essential oils, and pepper oil extract. The method of preparing the pain reliever oil includes marinating the dried flowers, the spices and the peppers in oil for specific times and under specific conditions. It is applied topically to relieve pain.

14 Claims, 2 Drawing Sheets

METHOD FOR MAKING A PAIN RELIEVER OIL

CROSS-REFERENCE TO RELATED APPLICATIONS

This application claims priority from U.S. Provisional Patent Application No. 62/415,643 filed on Nov. 1, 2016 which is hereby incorporated by reference.

STATEMENT REGARDING FEDERALLY SPONSORED RESEARCH

Not Applicable.

APPENDIX

Not Applicable.

BACKGROUND OF THE INVENTION

Field of the Invention

The present invention relates to a pain reliever compound, and more particularly to a pain reliever oil comprised of carrier oils, dried flowers, international assortment of hot peppers, and magnesium oil.

Related Art

There have been many alternative remedies for creating a pain relieving oil. However, most of the remedies only utilize certain ingredients over others rather than a combination of multiple known pain relieving ingredients.

SUMMARY OF THE INVENTION

A pain reliever oil comprised of carrier oils, dried flowers, leaves, roots, essential oils, hot peppers, and magnesium oil. The pain reliever oil ingredients are marinated or mixed in oil at various times to extract pain relieving chemicals. The final mixture is stored in a dark enclosure for a period of time.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings which are described in the detailed description.

DETAILED DESCRIPTION OF THE PREFERRED EMBODIMENTS

The following description of the preferred embodiment(s) is merely exemplary in nature and is in no way intended to limit the invention, its application, or uses.

Figure 1:
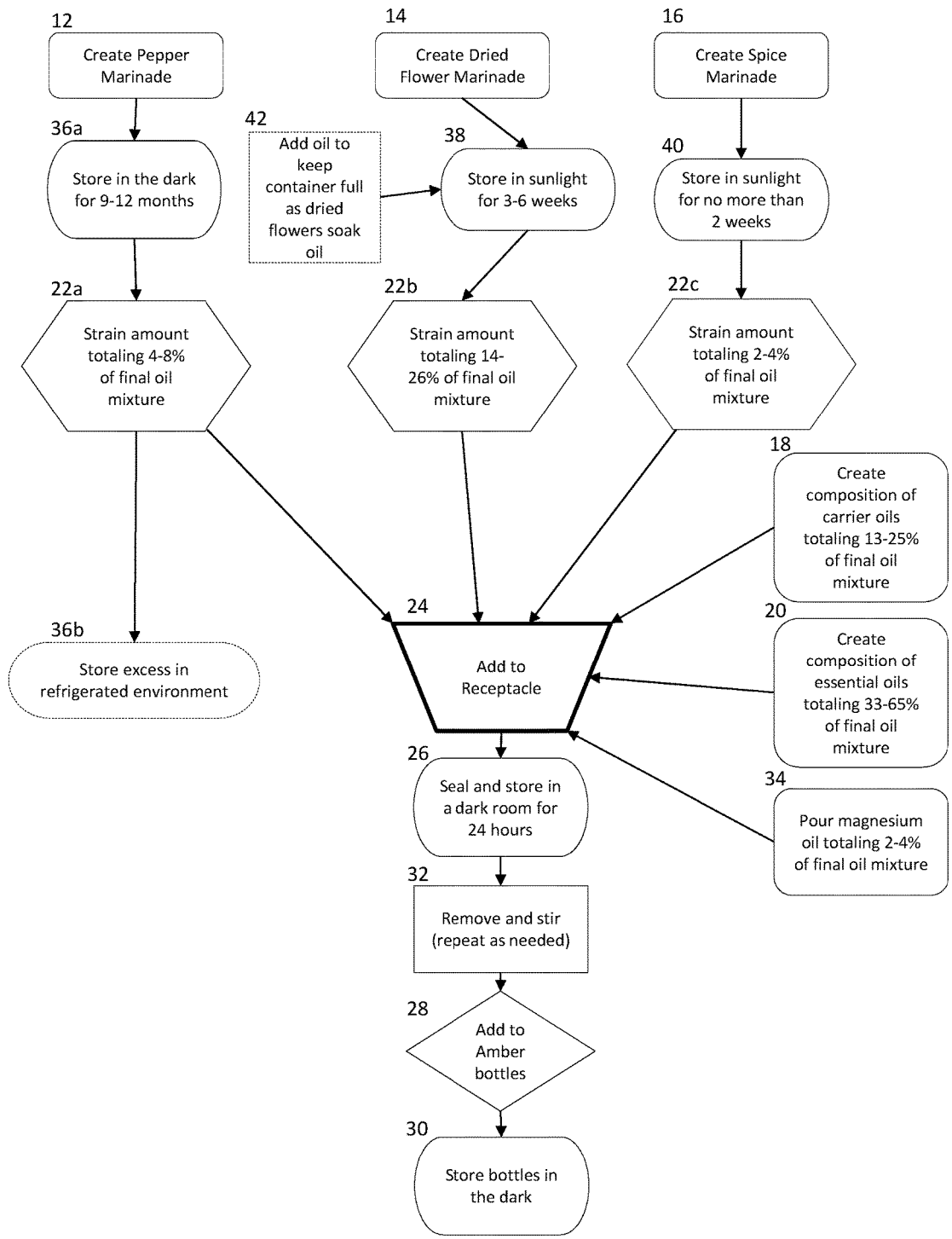
FIG. 1 is a flow chart of the preferred method of making the pain reliever oil.

In the preferred embodiment, the process 10 for creating the pain reliever oil begins by preparing oils, oil extracts, and three different marinades as shown in FIG. 1. The pepper marinade 12 is made up of a variety of peppers and is made by first drying the peppers and combining them with olive oil. Eight (8) ounces of each of the following peppers are used in the pepper marinade: Thai chilies, guajillo dry chilies, chile de árbol peppers, friggitelli, Fresno chilies, jalapeños, Mexican Thai hot peppers, and twisted Japanese chilies. Once dried, the dried peppers are added to one (1) gallon of cold pressed olive oil and the container holding the mixture of peppers and olive oil is stored in a dark room for nine (9) to twelve (12) months 36a. The container is preferably shaken once each week during the mixture's storage period. Due to the time that it takes to create the marinade from the mixture, a larger amount than is needed for a single batch of pain reliever oil is preferably made, and the unused remainder is preferably stored 36b in a refrigerator for preservation and later use.

In another aspect of the invention a flower marinade is made 14 for use within the pain reliever oil. The dried flower marinade is made by adding approximately two to three ounces (2-3 oz.) of dried flowers to a transparent twelve ounce (12 oz.) container and filling the container with olive oil. The dried flower marinade is made for each of five (5) flowers: calendula, *lavandula*, chamomile, *eucalyptus*, and plantains. In one method 2-3 ounces of each flower can be mixed in individual twelve ounce containers. Alternatively, the dried flowers may be mixed together before being placed into containers with each container having 2-3 ounces of the dried flower mixture. In another aspect of the flower marinade, the total amount of necessary flower marinade comes from five (5) containers with the five (5) marinade containers producing at least fifty ounces (50 oz.) of flower oil extract that is used in the pain reliever oil. Each container is preferably made from glass and is placed in sunlight for a period of three (3) to six (6) weeks 38. Although glass is preferred for the container and sunlight is preferred for the source of light and heating energy, it will be appreciated that a clear plastic container could be used and that grow lights and heat lamps may be used as an artificial source of light. The dried flower and oil mixture is monitored during the marinating period, and oil is added 42 to maintain volume as the dried flowers absorb the oil. Olive oil is typically added after one (1) to two (2) weeks of marinating.

In another aspect of the method for making the pain reliever oil, a spice marinade is prepared 16. The spice marinade is made of approximately four ounces (4 oz.) of turmeric root, approximately four ounces (4 oz.) of ginger root, approximately two ounces (2 oz.) of peppercorns and olive oil, collectively marinated in a twelve ounce (12 oz.) container. Similar to the process of making the flower marinade, the spices mixture is combined with olive oil in a clear container and left to set for period of time. However, the container with the spices and olive oil mixture is placed in the sun for no more than two (2) weeks 40, a shorter period of time than the flower mixture discussed above. The two-week limit for the oil and spice mixture is preferred because of the perishability of the plants.

The resulting three (3) marinades are filtered 22 to recover the oil extracts which are added to a receptacle to be mixed. The dried flower marinade is strained 22b through a cheese cloth to recover approximately ten ounces (10 oz.) of the dried flower oil extract from each of the five (5) containers (i.e., fifty ounces, 50 oz., in total). The strained flower oil can comprise between 14-26% of the final pain reliever oil. In the preferred embodiment the fifty ounces of flower oil is added to sixteen ounces (16 oz.) of the pepper marinade. In any embodiment the strained pepper oil extract 22a may range between 4-8% of the final pain reliever oil. Additionally, approximately eight ounces (8 oz.) of the spice oil extract is strained 22c from the spice marinade and combined with the flower and spice oils and makes up between 2-4% of the final pain reliever oil.

In addition to the three oils extracted from the marinades, a carrier oil mixture 18 comprised of eight ounces (8 oz.) each of castor oil, coconut oil, pure black castor oil, pure cold pressed black cumin seed oil, pure emu oil, unfiltered cold pressed oil is added into the mixing receptacle, and eight ounces (8 oz.) of magnesium oil is also added to the receptacle. The magnesium oil 34 can be a commercially available product or be created by dissolving or suspending four ounces (4 oz.) of magnesium chloride flakes in twelve ounces (12 oz.) of purified water for approximately 24 hours.

Figure 2:
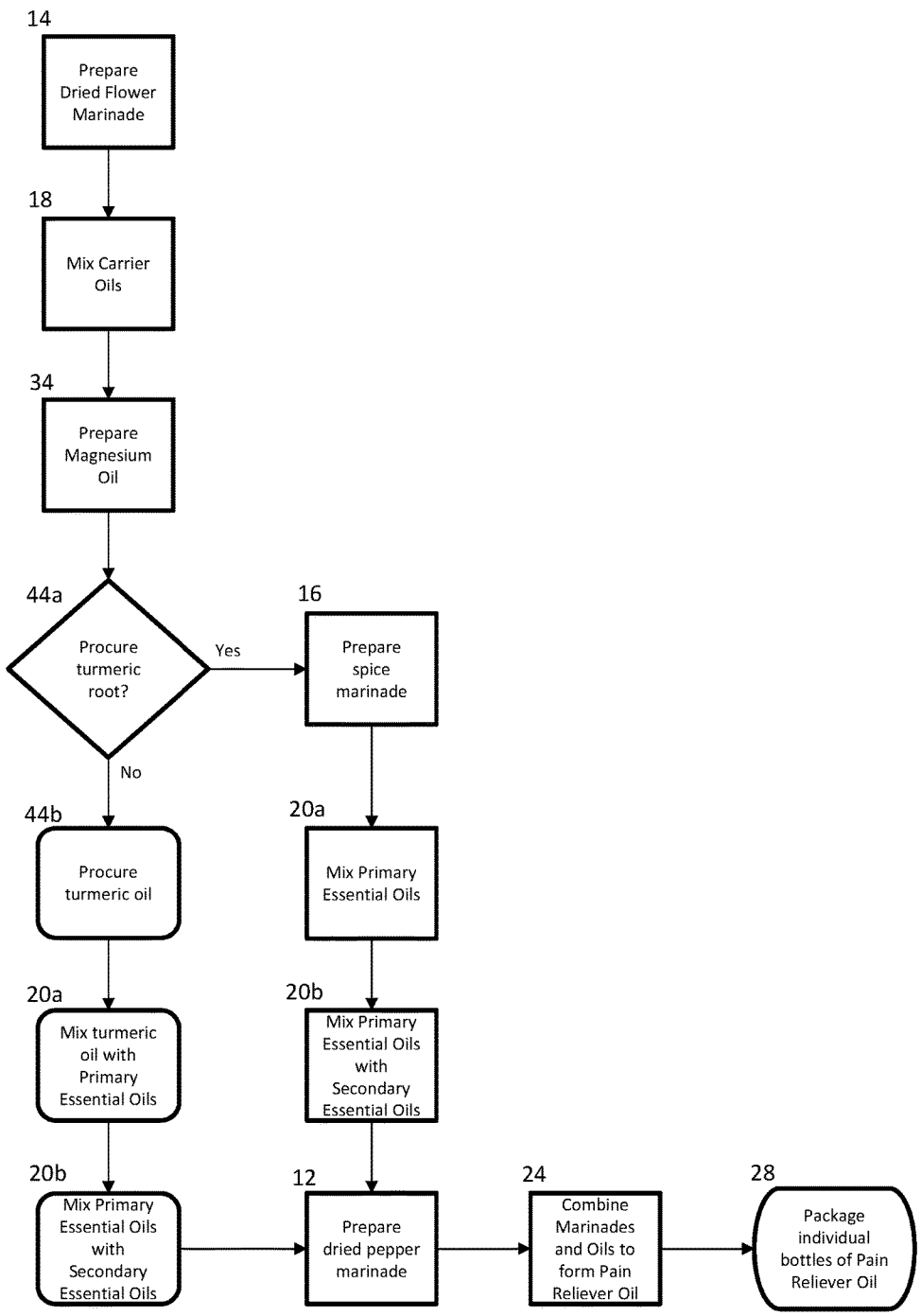
FIG. 2 is a flow chart of an alternative method of making the pain reliever oil.

A mixture of essential oils is also added to the receptacle 20. The essential oil mixture is comprised of two groups of essential oils. The first group is the primary essential oils is combined 20a and has eight ounces (8 oz.) each of wintergreen, black pepper oil, peppermint oil, clove oil, black spruce oil, camphor, and copaiba oil. Additionally, eight ounces of turmeric oil may be added to the primary essential oil mixture should turmeric root be unavailable when preparing the spice marinade, as illustrated in FIG. 2. The second group is the secondary essential oils combined 20b to have four ounces (4 oz.) each of benzoin, frankincense, sandalwood, cinnamon leaf, roman chamomile, tea tree oil, clary sage, sweet marjoram, juniper berry, ginger, tangerine, vetiver, helichrysum, rosemary, lemon, lavender, thyme, nutmeg, *eucalyptus*, and a preservative oil. In the preferred embodiment the preservative is GERMABEN II® but it will be appreciated by those having an ordinary skill in the art that other preservatives may effectively be substituted. The mixture of the oils results in an intermediate composition that undergoes further processing.

In an alternative method of making the pain reliever oil shown in FIG. 2, an optional step of procuring substitute oils for combination with the essential oil mixture may be taken when preparing the oil marinades. In some cases one or more raw ingredients used in the spice marinade, pepper marinade or flower marinade may not be readily available based on seasonal availability, demand, inflated pricing or for various other reasons. In such a case, the alternative method shown in FIG. 2 should be used where the missing raw ingredient is effectively replaced with a premade essential oil that can be sourced along with the other primary and secondary essential oils described herein. For example, turmeric root 44a is preferably used in the spice marinade but turmeric is a seasonal plant and may not always be readily available. If turmeric root is available the maker can proceed with making the spice marinade as described in the preferred embodiment. However, if turmeric root is unavailable turmeric oil should be substituted 44b and added to the primary essential oil mixture. Accordingly, turmeric oil may be added to the essential oil mixture in place of turmeric root used in the marinade depending on availability of the seasonal turmeric root.

Additionally, other essential oils may be sourced and used in the essential oil mixture in place of their corresponding raw ingredients in the marinades as descried with the turmeric root. Accordingly, FIG. 2 is an illustration of a single alternative method of making the pain reliever oil when turmeric root is unavailable but it should be appreciated that there are numerous alternative methods for making the pain reliever oil when one or more raw ingredients used in the marinades cannot be procured.

After the intermediate composition is mixed together 24, the receptacle is sealed and allowed to sit in a dark room for approximately twenty-four (24) hours 26. After the intermediate composition sits for one day, it is stirred again and again allowed to in a dark room for another twenty-four (24) hour period 32. This stir and sit process may again be repeated to produce a homogenous consistency results in the pain reliever oil. Immediately prior to filling storage bottles with the pain reliever oil, such as by pouring, siphoning, or depositing the oil, the pain reliever mixture is again stirred to ensure that a homogenous mixture fills each bottle, particularly including any sediments that are suspended in the oils and the magnesium oil which is a water-based mixture. Subsequently, the pain reliever oil is poured from the mixing receptacle into smaller storage bottles 28 more suitable for distribution. The storage bottles are preferably amber colored bottles to limit the light that reaches the pain reliever oil, and the bottles are preferably stored in a dark enclosure 30.

The composition of the pain reliever oil is not limited to the above measurements. As shown in the table below, the composition can vary.

| Composition | Preferred (oz.) | Preferred (%) | Range (%) |
| --- | --- | --- | --- |
| Spice marinade Oil Extract | 8 oz. | 3.1% | 2-4% |
| Magnesium Oil | 8 oz. | 3.1% | 2-4% |
| Pepper Marinade Oil Extract | 16 oz. | 6.3% | 4-8% |
| Carrier Oils | 48 oz. | 18.9% | 13-25% |
| Dried Flower Marinade Oil Extract | 50 oz. | 19.7% | 14-26% |
| Essential Oils | 124 oz. | 48.9% | 33-65% |
| Total | 254 oz. | 100% | |

According to the process described above, a pain reliever oil is made from a mixture of a dried flower oil extract, carrier oils, magnesium oil, spice oil extract, essential oils, and a capsaicin oil extract. The capsaicin oil extract is recovered from the marinade of any combination of the hot peppers in cold pressed olive oil as described above. Additionally, as explained in the description of the process above, in producing the marinade, the container holding the mixture of the hot peppers and the olive oil is placed in a dark room for nine (9) to twelve (12) months. Additionally, the other extracts and oils are mixed together according to the steps recited in the process for making the pain reliever oil and in the various relative amounts as set forth in the table above.

The embodiments were chosen and described to best explain the principles of the invention and its practical application to persons who are skilled in the art. As various modifications could be made to the exemplary embodiments, as described above regarding the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method for producing a pain reliever oil, comprising:
creating a pepper marinade from a composition of peppers containing capsaicin in cold pressed olive oil stored in a dark room for 9 to 12 months;
creating a dried flower marinade from a composition of dried flowers in cold pressed olive oil in sunlight, wherein the container is transparent or translucent;
creating a spice marinade from a composition of spices in olive oil stored in sunlight;
creating a mixture of carrier oils;
creating a mixture of essential oils;
recovering the oil extract of each of the pepper marinade, the dried flower marinade, and the spice marinade;
combining the recovered oil extracts, the mixture of carrier oils and the mixture of essential oils to create an intermediate composition;
wherein the intermediate composition comprises 4-8% pepper oil extract, 14-26% dried flower oil extract, 2-4% spice oil extract, 13-25% carrier oils, 33-65% essential oils and 2-4% magnesium oil;
covering and placing the receptacle in the dark for a period of approximately 24 hours to create the pain reliever oil; and
pouring the pain reliever oil into a bottle.

2. The method of claim 1 further comprising the steps of repetitively stirring the contents of the receptacle, storing the contents for approximately another 24 hours, and storing the bottle in the dark, and wherein the bottle is an amber bottle.

3. The method of claim 1, wherein the peppers are selected from the group consisting of capsaicin-containing peppers consisting of Thai Chilies, guajillo dry chilies, chile de árbol peppers, friggitelli, Fresno chilies, jalapeños, Mexican Thai hot peppers, twisted Japanese chilies and combinations thereof.

4. The method of claim 1, wherein the peppers are mixed with the Cold Pressed Olive Oil at a ratio of 1:2.

5. The method of claim 1, wherein the dried flowers are comprised of a selection of calendula, *lavandula*, chamomile, *eucalyptus*, and plantain mixed in a container.

6. The method of claim 1, wherein dried flowers are marinated in sunlight for 3 to 6 weeks.

7. The method of claim 1, wherein the spices are comprised of turmeric root, approximately 4 ounces of ginger root, and approximately 2 ounces of peppercorns.

8. The method of claim 1, wherein the carrier oils are comprised of an equal mixture of a selection from the group of oils consisting of Castor Oil, Coconut Oil, Pure Black Castor Oil, Pure Cold Pressed Black Cumin Seed Oil, Pure Emu Oil, Unfiltered Cold Pressed Oil, and any combination thereof.

9. The method of claim 1, wherein the essential oils are comprised of a 2:1 mixture of a primary essential oils and a secondary essential oil.

10. The method of claim 9, wherein the primary essential oils are comprised of wintergreen, black pepper, peppermint, cloves, black spruce, camphor, and copaiba oil, and wherein the secondary essential oils are comprised of benzoin, frankincense, sandalwood, cinnamon leaf, roman chamomile, tea tree oil, clary sage, sweet marjoram, juniper berry, ginger, tangerine, vetiver, helichrysum, rosemary, lemon, lavender, thyme, nutmeg, *eucalyptus*, turmeric oil and a preservative.

11. A method for producing a pain reliever oil, comprising:
creating a pepper marinade from a composition of peppers containing capsaicin in cold pressed olive oil stored in a dark room for 9 to 12 months;
creating a dried flower marinade from a composition of dried flowers in cold pressed olive oil stored in sunlight for 3 to 6 weeks, wherein the container is transparent or translucent;
creating a spice marinade from a composition of spices in olive oil stored in sunlight for 3 to 6 weeks;
creating a mixture of carrier oils;
creating a mixture of essential oils;
recovering the oil extract of each of the pepper marinade, the dried flower marinade, and the spice marinade;
combining the recovered oil extracts, the mixture of carrier oils and the mixture of essential oils to create an intermediate composition;
wherein the intermediate composition comprises 4-8% pepper oil extract, 14-26% dried flower oil extract, 2-4% spice oil extract, 13-25% carrier oils, 33-65% essential oils and 2-4% magnesium oil;
covering and placing the receptacle in the dark for a period of approximately 24 hours to create the pain reliever oil; and
pouring the pain reliever oil into a bottle.

12. The method of claim 11, wherein the peppers are selected from the group of capsaicin-containing peppers consisting of Thai chilies, guajillo dry chilies, chile de arbol peppers, friggitelli, Fresno chilies, jalapenos, Mexican Thai hot peppers, twisted Japanese chilies and combinations thereof, wherein the dried flowers are comprised of a selection of calendula, *lavandula*, chamomile, and *eucalyptus* and wherein the spices are comprised of approximately 4 ounces turmeric root, approximately 4 ounces of ginger root, and approximately 2 ounces of peppercorns.

13. The method of claim 11, wherein the carrier oils are comprised of an equal mixture of a selection from the group of oils consisting of Castor Oil, Coconut Oil, Pure Black Castor Oil, Pure Cold Pressed Black Cumin Seed Oil, Pure Emu Oil, Unfiltered Cold Pressed Oil, and any combination thereof.

14. The method of claim 11, wherein the essential oils are comprised of a 2:1 mixture of a primary essential oils and a secondary essential oil, wherein the primary essential oils are comprised of wintergreen, black pepper, peppermint, cloves, black spruce, camphor, and copaiba oil, and wherein the secondary essential oils are comprised of benzoin, frankincense, sandalwood, cinnamon leaf, roman chamomile, tea tree oil, clary sage, sweet marjoram, juniper berry, ginger, tangerine, vetiver, helichrysum, rosemary, lemon, lavender, thyme, nutmeg, *eucalyptus*, turmeric oil and a preservative.

* * * * *